(12) United States Patent
Shoji et al.

(10) Patent No.: US 9,730,787 B2
(45) Date of Patent: Aug. 15, 2017

(54) SOFT INTRAOCULAR LENS

(75) Inventors: Noriyuki Shoji, Kitamoto (JP);
Masanobu Inoue, Honjo (JP)

(73) Assignee: Hoya Corporation, Tokyo (JP)

( * ) Notice: Subject to any disclaimer, the term of this patent is extended or adjusted under 35 U.S.C. 154(b) by 244 days.

(21) Appl. No.: 12/441,983

(22) PCT Filed: Oct. 1, 2007

(86) PCT No.: PCT/JP2007/069223
§ 371 (c)(1),
(2), (4) Date: Jan. 16, 2010

(87) PCT Pub. No.: WO2008/041683
PCT Pub. Date: Apr. 10, 2008

(65) Prior Publication Data
US 2010/0145446 A1   Jun. 10, 2010

(30) Foreign Application Priority Data
Oct. 4, 2006 (JP) .................................. 2006-273449

(51) Int. Cl.
*A61F 2/16* (2006.01)

(52) U.S. Cl.
CPC .... *A61F 2/1613* (2013.01); *A61F 2002/1681* (2013.01); *A61F 2002/1683* (2013.01);
(Continued)

(58) Field of Classification Search
CPC ...... A61F 2002/1681; A61F 2002/1683; A61F 2002/1686; A61F 2/1613; A61F 2002/16905
(Continued)

(56) References Cited

U.S. PATENT DOCUMENTS 4,615,702 A   10/1986   Koziol
4,725,277 A   2/1988   Bissonette
(Continued)

FOREIGN PATENT DOCUMENTS

EP   0195881 A1   10/1986
EP   0413057 A1   8/1989
(Continued)

OTHER PUBLICATIONS

PCT International Search Report dated Oct. 23, 2007 for PCT App. Ser. No. PCT/JP2007/069223.
(Continued)

*Primary Examiner* — Howie Matthews
(74) *Attorney, Agent, or Firm* — Henricks, Slavin & Holmes LLP

(57) ABSTRACT

An intraocular lens of the present invention has a substantially circular or elliptical optical lens portion made of a soft material, and an arm-shaped support arm portion attached to outer peripheral edges of this optical lens portion, and out of the peripheral edges of the optical lens portion that are contiguous to both sides in a width direction of a root of the support arm portion, at least one outer peripheral edge has a portion recessed inward from the convex curve. Thus, there is provided a soft intraocular lens that can be inserted into an eye from a further smaller incision, without damaging an optical function as much as possible.

14 Claims, 5 Drawing Sheets

(52) U.S. Cl.
CPC .............. *A61F 2002/16905* (2015.04); *A61F 2250/0018* (2013.01)

(58) Field of Classification Search
USPC ....................................... 623/6.11, 6.21, 6.46
See application file for complete search history.

(56) References Cited

U.S. PATENT DOCUMENTS

| | | | |
|---|---|---|---|
| 4,764,169 A | 8/1988 | Grendahl | |
| 5,015,254 A | 5/1991 | Greite | |
| 5,135,540 A * | 8/1992 | Schepel et al. | 623/6.46 |
| 5,217,491 A | 6/1993 | Vanderbilt | |
| 5,266,241 A | 11/1993 | Parekh | |
| 5,589,024 A | 12/1996 | Blake | |
| 5,618,316 A | 4/1997 | Hoffman | |
| 5,674,282 A | 10/1997 | Cumming | |
| 5,716,403 A | 2/1998 | Tran | |
| 6,193,750 B1 | 2/2001 | Cumming | |
| 6,267,784 B1 * | 7/2001 | Benz et al. | 623/6.59 |
| 6,310,215 B1 | 10/2001 | Iwamoto | |
| 6,342,073 B1 * | 1/2002 | Cumming et al. | 623/6.46 |
| 6,387,127 B1 * | 5/2002 | Muller-Lierheim | 623/6.59 |
| 6,555,030 B1 * | 4/2003 | Weinschenk, III | 264/1.7 |
| 6,942,695 B1 | 9/2005 | Chapoy | |
| 7,160,488 B2 | 1/2007 | Ichikawa | |
| 7,223,288 B2 | 5/2007 | Zhang | |
| 7,632,431 B2 * | 12/2009 | Ghazizadeh et al. | 264/1.7 |
| 2003/0158560 A1 | 8/2003 | Portney | |
| 2004/0111151 A1 | 6/2004 | Paul | |
| 2009/0082861 A1 | 3/2009 | Marunaka | |
| 2011/0313520 A1 | 12/2011 | Shoji | |

FOREIGN PATENT DOCUMENTS

| | | |
|---|---|---|
| EP | 0 172 618 A2 | 2/2015 |
| FR | 2773705 A1 | 7/1999 |
| JP | 4-502586 A | 5/1992 |
| JP | 4-295353 A | 10/1992 |
| JP | 8-501480 | 2/1996 |
| JP | 9-276303 A | 10/1997 |
| JP | 10-043214 A | 2/1998 |
| JP | 10-85319 A | 4/1998 |
| JP | 10-192311 | 7/1998 |
| JP | 10-513099 A | 12/1998 |
| JP | 2000-290256 A | 10/2000 |
| JP | 2002-540828 A | 12/2002 |
| JP | 2003-511197 A | 3/2003 |
| JP | 2006-231066 A | 9/2006 |
| WO | WO 90/04512 A1 | 5/1990 |
| WO | WO95/01762 A | 1/1995 |
| WO | WO 97/20523 A1 | 6/1997 |
| WO | WO 00/59365 A | 10/2000 |
| WO | WO 01/28458 A | 4/2001 |
| WO | WO 2006/123428 A1 | 11/2006 |

OTHER PUBLICATIONS

EPO Supplementary Search Report dated Nov. 8, 2013 for EPO App. Ser. No. 07828963.4.

* cited by examiner

SOFT INTRAOCULAR LENS

TECHNICAL FIELD

The present invention relates to a soft intraocular lens inserted into an aphakic eye after cataract surgery, or relates to a soft intraocular lens for a phakic eye inserted into an eye in a refraction correction surgery.

DESCRIPTION OF RELATED ART

For example, when a crystal lens is cloudy by cataract, recovery of lost vision is attempted by a surgical procedure such as inserting an intraocular lens, being an artificial lens, into an eye, instead of this cloudy crystal lens.

The intraocular lens used at this time has a substantially circular or elliptical optical lens, and a support arm portion extending outward of outer peripheral edges of the optical lens portion so as to make this optical lens stable in the eye.

In recent years, silicon resin, acrylic resin, and hydrogel, etc, have been used as materials of the optical lens, and a soft intraocular lens that can be deformed (folded) is provided. This soft intraocular lens can be inserted into the eye in a state of folding the optical lens portion. Therefore, an incision during surgery can be made small, and this contributes to many clinical advantages such as early recovery after surgery.

Also, in order to insert a lens into the eye, a dedicated injector having a structure of introducing the lens into the eye through a slender tube is sometimes used. By using an injector only for such an intraocular lens, the lens can be inserted from the incision smaller than 3 mm.

In order to insert the intraocular lens from a further smaller incision, various improvement of the injector has been performed heretofore. For example, there are techniques such as applying surface treatment to an inner wall of an intraocular lens passage of the injector, to thereby make the pass of the intraocular lens smooth (see patent document 1), and such as designing a shape of the inner wall of the intraocular lens passage of the injector so as to be suitable for controlling a folding behavior of the intraocular lens in the passage (see patent document 2). However, there is a limit only by improvement of the injector, thus posing a problem that the intraocular lens is jammed in a passage, or the intraocular lens released from the passage is broken.

Meanwhile, in order to respond to a smaller incision, the intraocular lens itself is variously devised. For example, patent document 3 discloses a technique of making the thickness of a lens itself thinner, by dividing the intraocular lens into several stepwise annular rings.

Patent document 1: Japanese Translation of PCT international patent application No. 2000-514333
Patent document 2: Japanese Translation of PCT international patent application No. 2002-541912
Patent document 3: Japanese Translation of PCT international patent application No. 2004-535251

DISCLOSURE OF THE INVENTION

Problem to be Solved by the Invention

However, in the aforementioned patent document 3, as a result of making the intraocular lens thinner, although the intraocular lens can be inserted from a significantly small incision, there is possibly a problem that an optical function such as hallows is damaged, because an optical surface is divided in a shape of stairs.

An object of the present invention is to provide a foldable soft intraocular lens that can be inserted from a further smaller incision, without damaging an optical function as much as possible.

Means to Solve the Invention

As a result of repeating sufficient observation and analysis on a behavior of folding up an intraocular lens in an injector, it is found by inventors of the present invention that jamming of the intraocular lens in the injector, thereby damaging the lens in a passage, is caused in many cases by mutual interaction between a support arm portion and an optical lens portion of the intraocular lens in a process of folding up the intraocular lens in an injector passage, or in a process of advancement of the folded intraocular lens in the passage; by mutual interaction between outer peripheral edges of the optical lens portion in a state of being folded into two; by mutual interaction among the support arm portion, the optical lens portion, and an inner wall of the injector passage; or by a manner of force transmission from a plunger to the vicinity of a root of the support arm portion when the intraocular lens is pressed by the plunger of the injector. Also, on the basis of the aforementioned knowledge and as a result of analyzing breakage or crack and a generation part of the other trouble and a broken shape, the inventors of the present invention achieves the present invention.

A first invention provides a soft intraocular lens, having:
an optical lens portion having a substantially circular or elliptical optical lens portion made of a foldable soft material; and
a support arm portion formed into an arm shape, extending outward from outer peripheral edges of this optical lens portion, for retaining/fixing the optical lens portion in an eye,
wherein a major part of an outer circumference contour lines of the optical lens portion is formed so as to be placed on a continuous convex curve, and out of the peripheral edges of the optical lens portion that are contiguous to both sides in a width direction of the root of the support arm portion, at least one outer peripheral edge has a portion recessed inward from the convex curve, with one end of this recessed portion continued to the outer circumference contour lines of the optical lens placed on the convex curve, and the other end of this recessed portion continued to the contour lines of an outer edges in the width direction of the root of the support arm portion.

A second invention provides the soft intraocular lens according to the first invention, wherein the recessed portion is provided on both sides in the width direction of the root of the support arm portion.

A third invention provides the soft intraocular lens according to the first invention or the second invention, wherein the support arm portion and the optical lens portion are integrally formed one piece type, and the support arm portion is made of a material harder than a soft material constituting the optical lens portion.

A fourth invention provides the soft intraocular lens according to the third invention, wherein by providing the recessed portion, a substantial root position of the support arm portion is changed to an inner peripheral side from an initial root position before the recessed portion is provided, and a boundary between the soft material and the hard material is substantially located at the outer peripheral side of the substantial root position of the support arm portion. Here, the inner peripheral side means the side closer to a center of the optical lens portion, and the outer peripheral side means the side farther from the center of the optical lens portion.

A fifth invention provides the soft intraocular lens according to the fourth invention, wherein by forming inside of the convex curve by the soft material, and forming outside of the convex curve by the hard material, with the convex curve set as the boundary, an area from the initial root to a tip end of the support arm portion is made of the hard material, and an area including the optical lens portion inside of the initial root of the support arm portion is made of the soft material.

Advantage of the Invention

According to the first invention, out of the peripheral edges of the optical lens portion of both sides of the root of the support arm portion, at least one outer peripheral edge of the optical lens portion has the recessed portion. Therefore, when a case of having two support arm portions at positions that are point symmetric with each other, is taken as an example, a stress generated in the root of the support arm portion can be alleviated when folding up the intraocular lens, with the support arm portion positioned at both ends in an axial direction of a folding axis (this folding is called a "vertical folding", and also flexibility in the vicinity of the root can be increased. Accordingly, it is possible to prevent the crack from occurring in the root.

In addition, by providing the recessed portion, it is possible to alleviate mutual interaction of outer peripheral edges of the optical lens portion when folded into two. Namely, when the mutual interaction occurs between the outer peripheral edges of the optical lens at the time of folding the optical lens, there is a possibility that damage is added to the vicinity of the root of the support arm portion, and this damage possibly relates to a generation of the crack in the root of the support arm portion. However, this mutual interaction can be alleviated and this contributes to preventing the generation of the crack.

Accordingly, the intraocular lens can be released into the eye without difficulty, through a thin injector passage, with less damage.

According to the second invention, the recess portion is provided on both sides in a width direction of the root of the support arm portion. Therefore, not only in a case of vertically folding the intraocular lens, but also in a case of horizontally folding the intraocular lens, the aforementioned problem due to mutual interaction can be solved. In addition, when the recess portion is provided on both sides, a relatively greater flexibility can be added to the periphery of the root of the support arm portion. Therefore, from this point also, the damage of the intraocular lens can be decreased. Note that a "horizontal folding" means the folding of the intraocular lens, with a folding axis orthogonal to the folding axis of a vertical folding as a reference.

According to the third invention, since the optical lens portion and the support arm portion are integrally formed, machining accuracy of the support arm portion can be easily increased. In addition, since the support arm portion is hard, it is possible to increase stability at the time of inserting the lens into the eye (capsule). Also, when the optical lens portion and the support arm portion are formed of materials of different kind, there is a weak point that a bonding strength in a boundary part of the materials of different kind is easily weakened. However, by providing the recess portion on at least one side of the root of the support arm portion, the flexibility in the vicinity of the root of the support arm portion, namely in the vicinity of the boundary part between the materials of different kind, can be increased. Thus, the weak point in terms of strength can be complemented.

According to the fourth invention, by providing the recess portion, a substantial root position of the support arm portion is changed to an inner peripheral side of an initial root position before the recess portion is provided, and also the boundary between a soft material and a hard material is set on an outer peripheral side of the substantial root position of the support arm portion. Therefore, the flexibility in the periphery of the root of the support arm portion can be further increased.

According to the fifth invention, by forming an area inside of the convex curve defining outer peripheral contours of the optical lens portion by the soft material, and forming an area outside thereof by the hard material, an area from an initial root of the support arm portion before the recess portion is provided, to the substantial root of the support arm portion after the recess portion is provided, is made of the same soft material as the material of the optical lens portion. Therefore, by polymerizing a hard resin and a soft resin, with the convex curve set as the boundary, and by cut-out from this polymerized material, it is possible to easily manufacture the intraocular lens including the recess portion on the outer peripheral edges of the optical lens portion.

BEST MODE FOR CARRYING OUT THE INVENTION

Preferred embodiments of the present invention will be described hereunder, with reference to the drawings.

FIG. 1(a) is a front view of an intraocular lens of an embodiment, FIG. 1(b) is a side view, and FIG. 2 is an expanded view of an essential part of the intraocular lens.

As shown in FIG. 1, this intraocular lens 1 includes an optical lens portion 10 made of a foldable soft acrylic material, and two curve-shaped support arm portions 20 (or "haptics") made of polymethylmethacrylate (PMMA), being a harder material than the material of the optical lens portion 10, and the optical lens portion 10 is formed as a circular convex lens.

The support arm portion 20 is a portion to retain/fix the optical lens portion 10 in an eye, and two support arm portions 20 are provided so as to be point symmetry, with a center O of the optical lens portion 10 set as a center. As shown in FIG. 2, a plan shape of each support arm portion 20 is formed into a shape that obliquely extends toward one side in a circumferential direction of the optical lens portion 10 from a point on outer peripheries of the optical lens portion 10, and curved from its root 21A to a tip end 22, toward one side in the circumferential direction of the optical lens portion 10. Specifically, the support arm portion 20 is formed into a curved shape wherein a ratio of being away from the optical lens portion 10 is decreased as it goes outward from the root 21A, being the vicinity of the boundary between the support arm portion 20 and the optical lens portion 10, and approximately a concentric relation with the optical lens portion 10 is made in the vicinity of the tip end 22.

In addition, a major part of the outer peripheral contours 11 of the optical lens portion 10 is formed so as to be placed on a continuous convex curve (outer periphery of a circle or outer periphery of an ellipse) 30, and smooth recess portions 12, 13 recessed to the inside of the convex curve 30 are provided on outer peripheral edges of the optical lens portion 10 that are contiguous to both sides in a width direction of the root 21A of the support arm portion 20.

Then, one end (end portion at a position farther from the support arm portion 20) of these recess portions 12, 13 is continued to the outer peripheral contours 11 of the optical lens portion 10 placed on the convex curve 30, and the other end of the recess portions 12, 13 (end portion at a position closer to the support arm portion 20) is continued to contour lines 20a, 20b of outer edges in a width direction of the root 21A of the support arm portion 20, via a smooth curve.

In this case, when the root of the support arm portion 20 positioned on the convex curve 30 before the recess portions 12, 13 are formed, is set as an initial root 21A, a substantial root 21B of the support arm portion 20 is changed to a position on a line connecting bottoms of the recess portions 12, 13 of both sides, by providing the recess portions 12, 13. Then, by forming inside of the convex curve 30 by a soft material (soft acrylic material), and by forming outside of the convex curve 30 by a hard material (PMMA), an area from the initial root 21A to the substantial root 21B is made of the same soft material as the material of the optical lens portion 10.

In addition, as shown in FIG. 1(b), a side-view shape of the support arm portion 20 is formed so that an area closer to a tip end 22 is almost parallel to a plan face orthogonal to an optical axis, by providing two folded portions 20s, 20t which are mutually directed in opposite directions. Here, an angle is formed by a straight line connecting the tip end 22 of the support arm portion 20 and outer peripheral end portions of the optical lens portion 10, and the plan face orthogonal to the optical axis. This angle is set to be θ. In this case, θ is set to be, for example, about 5°.

According to the intraocular lens 1 constituted as described above, the recess portions 12, 13 are provided on the outer peripheral edges of the optical lens portion 10 on both sides of the root 21A of the support arm portion 20. Therefore, when the intraocular lens 1 is vertically folded, with the Y-axis of FIG. 1 set as a reference, a stress particularly generated outside can be alleviated, and the flexibility in the vicinity of the root 21A can be increased. Accordingly, it is possible to prevent a crack from generating in the root 21A.

In addition, by providing the recess portions 12, 13, it is possible to alleviate mutual interaction of the outer peripheral edges of the optical lens portion 10 when the intraocular lens 1 is folded into two. Namely, when the mutual interaction of the outer peripheral edges of the optical lens portion occurs when the intraocular lens 1 is folded, there is a possibility that damage is added to the vicinity of the root 21A of the support arm portion 20. However this damage can be avoided. This contributes to prevention of the crack in the vicinity of the root 21A of the support arm portion 20.

Accordingly, the intraocular lens 1 can be released into an eye without difficulty, through a thin injector passage, with less damage.

In addition, by providing the recess portions 12, 13 on both sides in the width direction of the root 21A of the support arm portion 20, not only in a case of vertically folding the intraocular lens 1, but also in a case of horizontally folding the intraocular lens 1, and also in a case of folding the intraocular lens in a middle of vertical and horizontal folding, a problem due to the mutual interaction can be solved. Here, a "horizontal folding" means folding of the intraocular lens 1, with the X-axis set as a reference. Note that when the intraocular lens is folded, with the Y-axis set as a reference, the mutual interaction of the optical lens portion 10 easily occurs in a part where the recess portion 12 is provided. Namely, the mutual interaction of the optical lens portion 10 occurs at a part in the vicinity of the root of the support arm portion 20, and at a part positioned opposite to the side where the support arm portion 20 is curved toward the optical lens portion 10. Therefore, when rigidity of the support arm portion 20 is particularly desired to be made strong, preferably the recess portion 13 is not provided and only the recess portion 12 is provided (see lens 1a in FIG. 5).

In addition, one piece type, in which the support arm portion 20 and the optical lens portion 10 are integrally formed, is provided, and therefore machining accuracy of the support arm portion 20 can be easily increased. In addition, the support arm portion is hard, and therefore stability at the time of inserting the lens into the eye (capsule) can be increased. Also, it is possible to suppress a phenomenon that jamming occurs due to twisting of the support arm portion 20, when passed through the injector. Further, when the optical lens portion 10 and the support arm portion 20 are formed by materials of different kind, there is a weak point that bonding strength in a boundary part of materials of different kind is weakened. However, by providing the recess portions 12, 13 on both sides of the root of the support arm portion 20, it is possible to increase the flexibility in the vicinity of the root of the support arm portion 20, namely in the vicinity of the boundary part of the materials of different kind. Therefore, a weak point in terms of strength can be complemented, and durability at the time of folding the lens can be increased.

In addition, by providing the recess portions 12, 13 on the outer peripheral edges of the optical lens portion 10, a substantial root 21B of the support arm portion 20 is changed to a position corresponding to bottoms of the recess portions 12, 13, and an area from the initial root 21A to the substantial root 21B is made of the same soft material as the material of the optical lens portion 10. Therefore, the flexibility in the vicinity of the root of the support arm portion 20 can be increased.

FIG. 3(a) schematically shows a state that the intraocular lens 1 of an embodiment passes through an intraocular lens passage of a general injector 100, and shows a case that the intraocular lens 1 is folded up in the Y-axial direction of FIG. 1 (a case of vertical folding). The intraocular lens 1 inserted from an injector inlet (not shown) is pushed out to a tip end direction of the injector 100 by a plunger 105, and finally is released into the eye from an injector tip end opening 102.

In a process of being pushed out, the intraocular lens 1 is gradually folded-up into a small shape as shown in FIG. 3(b) and FIG. 3(c), while performing slide-contact with a passage inner wall 101. However, by providing the recess portions 12, 13 on the outer peripheral edges of the optical lens portion 10 of the intraocular lens 1, interaction between the vicinity of the root of the support arm portion 20 and outer peripheral parts of the optical lens portion 10 is suppressed. Therefore, a force added to a weak part of the intraocular lens 1, namely added to a connection part between the soft acrylic material and the PMMA material, is reduced. As a result, generation of breakage can be suppressed.

Moreover, by suppressing the interaction, not only the breakage of the connection part between two materials can be suppressed, but also the crack or damage of the optical lens portion 10 can be suppressed. Further, in this embodiment, as described above, a range from the initial root 21A to the substantial root 21B of the support arm portion 20 is made of the soft acrylic material. Therefore, the force added to the support arm portion 20 can be dispersed and transmitted to this area made of the soft acrylic material. This makes it possible to suppress the breakage of the support arm portion 20 itself.

Further, the recess portion 13 at the plunger 105 side can disperse/absorb a pressure generated when the outer peripheral edge parts of the optical lens portion 10 is pressed by the plunger 105. Therefore, it is possible to expect an effect of suppressing the breakage in the vicinity of the root of the support arm portion 20 at the plunger 105 side.

Note that the aforementioned description is given for a case that a direction of folding up the intraocular lens 1 in the injector 100 is the Y-axial direction (case of the vertical folding). However, the effect of suppressing the interaction by the recess portions 12, 13 can also be exhibited in a case that the intraocular lens 1 is folded up in the X-axial direction.

The intraocular lens 1 constituted as described above is a soft intraocular lens of one piece type in which the support arm portion 20 and the optical lens portion 10 are integrally formed, and is manufactured as follows.

First, as shown in FIG. 4(a), an approximately donut-shaped support arm portion constituting member 200 made of PMMA is obtained by using a publicly-known molding method. For example, a circular hole 201 is opened in a center part of a button material which is obtained by molding the PMMA into an approximately disc shape.

Next, a raw material liquid 250, becoming soft acryl after curing, is injected into the circular hole 201 in the center part of the support arm portion constituting member 200, and this raw material liquid 250 is cured, to thereby complete polymerization. Thus, as shown in FIG. 4(b), it is possible to obtain a disc-shaped raw material 300 in which a material 250 constituting an optical lens portion and a material 200 constituting a support arm portion are integrally formed.

Next, as shown in FIG. 4(c), surface forming work is applied to front/back surfaces of the disc-shaped raw material 300 by using a precision lathe working apparatus. Thus, an intermediate member 350 having a disc shape in plan view, in which a curved surface shape of the optical lens portion 10 and the front/back surface shape of the support arm portion are formed, but the support arm portion is not formed yet.

Next, as shown in FIG. 4(d), a contour shape in plan view as shown by solid line is formed by using a milling device. At this time, the recess portions 12, 13 are also formed by milling. Finally, polishing is performed, and the intraocular lens 1 of one piece type as shown in FIG. 1 is obtained.

Here, a specific example of dimension of the intraocular lens 1 shown in FIG. 1 is shown. M1 is for example set at 12.5 mm, M2 is for example set at about 6.0 mmϕ, M3 is for example set at 2.3 mm, M4 is for example set at 0.48 mm, M5 is for example set at 0.6 mm, M6 is for example set at 5.6 mm, curvature R1 of the recess portion 12 is for example set at 0.6 mm, and curvature R2 of the recess portion 13 is for example set at 0.3 mm.

As the other examples of soft materials of the optical lens portion 10, a silicone-based material and hydrogel, etc, can be given, and as the other examples of materials of the support arm portion 20, acrylic-based material, polyamide, and polypropylene, etc, can be given.

Note that efficiency can be particularly exhibited by the present invention, compared with the intraocular lens of one piece type in which the support arm portion 20 and the optical lens portion 10 are integrally formed of materials of different kind, which is relatively weak in connection between the support arm portion 20 and the optical lens portion 10. However, it is a matter of course that the present invention can be applied to the intraocular lens of one piece type in which the support arm portion 20 and the optical lens portion 10 are formed of the same material, and also can be applied to the intraocular lens of three piece type in which the support arm portion 20 and the optical lens portion 10 are separately formed and thereafter connected with each other by heat welding, etc.

The aforementioned embodiment shows a case that the area from the initial root 21A to the substantial root 21B is made of the same soft material as the material of the optical lens portion 10. However, it is also acceptable that the area from the initial root 21A to the substantial root 21B is made of the same hard material as the material of the support arm portion 20.

In this case also, a problem of interference during folding up the intraocular lens 1 can be suppressed, by an existence of contiguous recess portions 12, 13. Therefore, an effect of preventing damage particularly in the vicinity of the root of the support arm portion 20 can be exhibited.

Also the aforementioned embodiment shows a case that the recess portions 12, 13 are provided on both sides in a width direction of the root 21A of the support arm portion 20. However, even in a case that the recess portion 12 or the recess portion 13 is provided only on one side, and particularly in a case that the recess portion 12 is provided only outside in an obliquely extending direction of the support arm portion 20, a certain degree of the aforementioned effect can be exhibited.

BRIEF DESCRIPTION OF THE DRAWINGS

FIG. 1(a) is a front view, and FIG. 1(b) is a side view.

FIG. 3(a) is a vertical sectional view, FIG. 3(b) is a sectional view when an intraocular lens 1 passes through line IIIb-IIIb, and FIG. 3(c) is a sectional view when the intraocular lens 1 passes through line IIIc-IIIc of (a).

DESCRIPTION OF SIGNS AND NUMERALS

Figure 1:
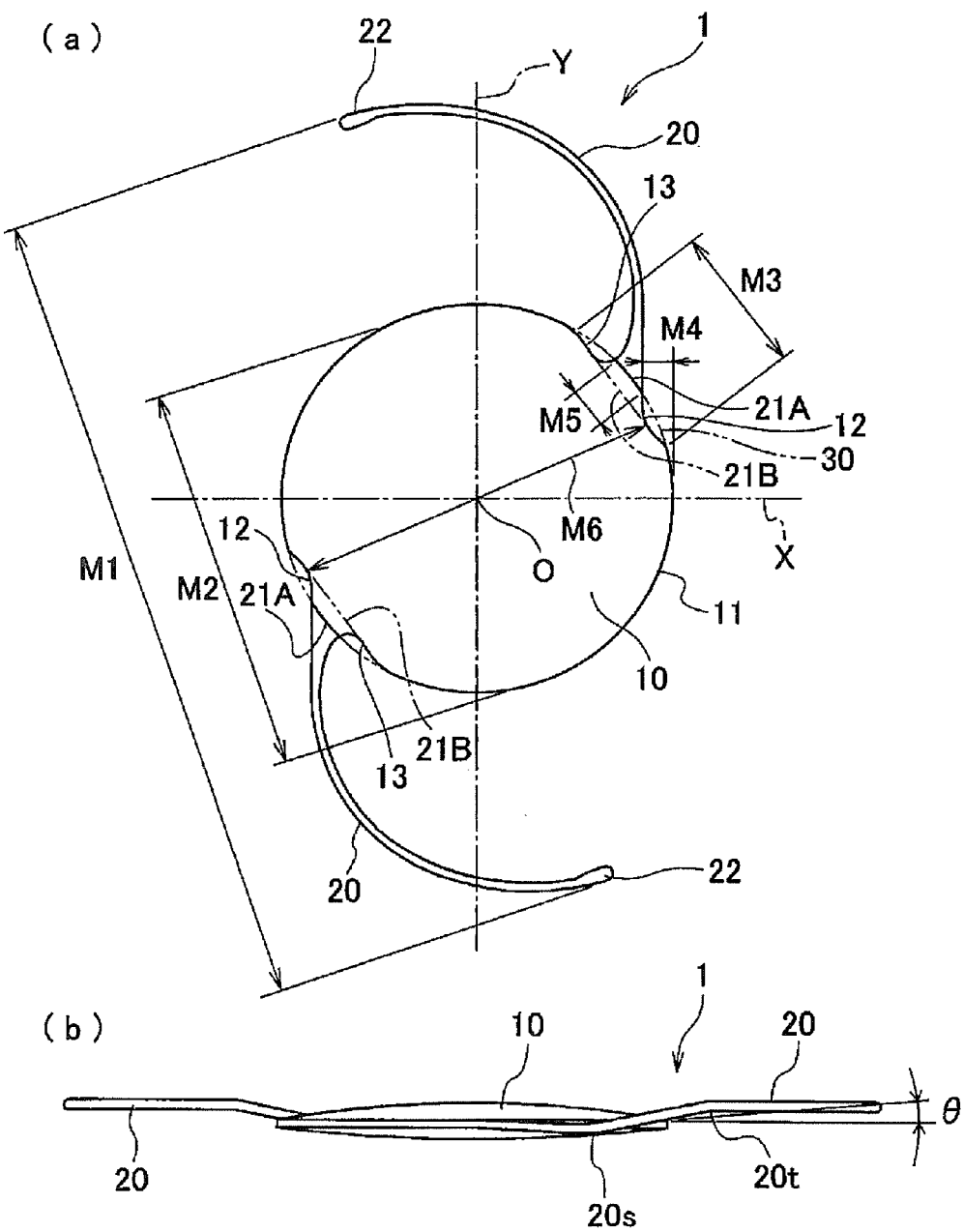
FIG. 1 is a block diagram of an intraocular lens according to an embodiment of the present invention.
Figure 2:
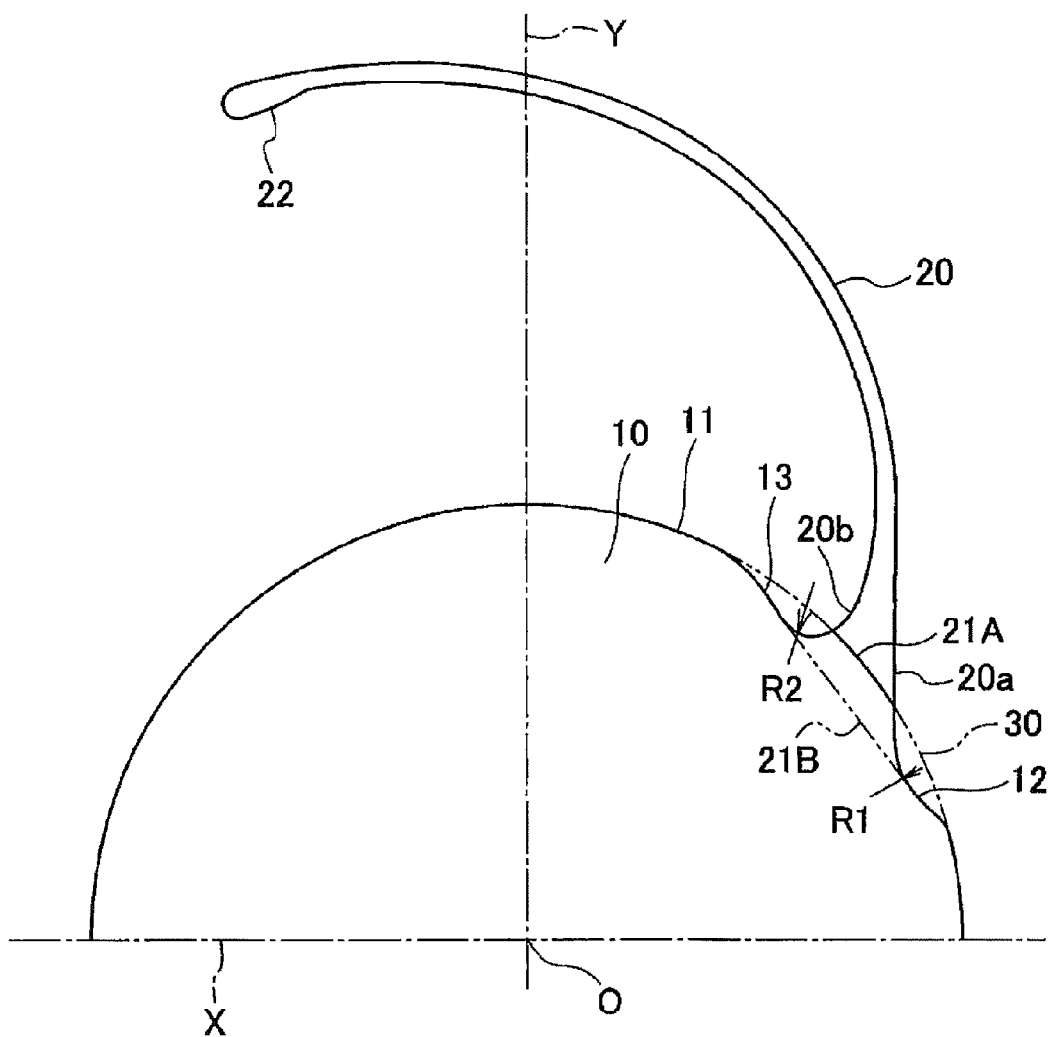
FIG. 2 is an expanded view of an essential part of the intraocular lens.
Figure 3:
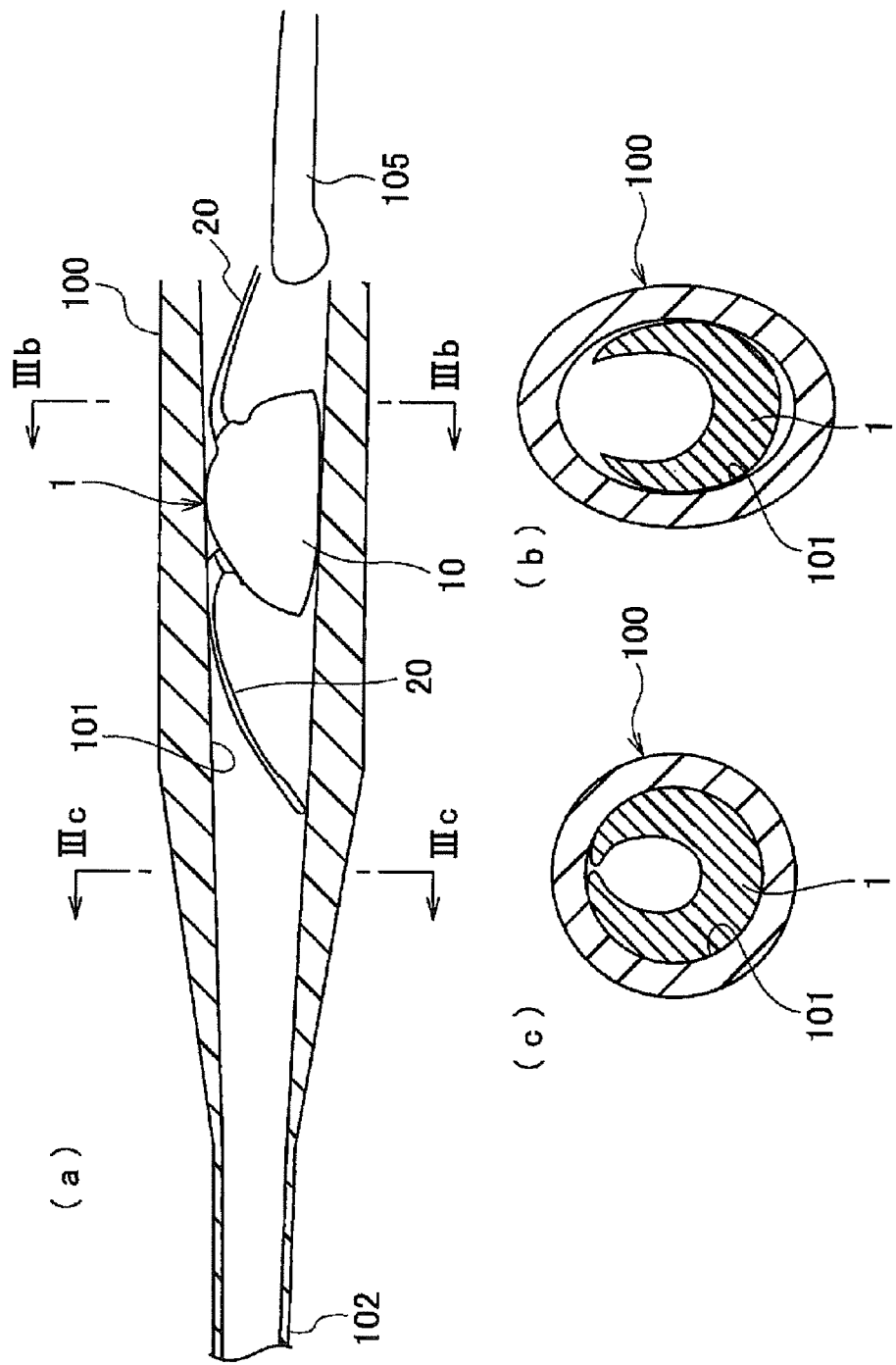
FIG. 3 is a schematic view in a case of passing the intraocular lens through an injector.
Figure 4:
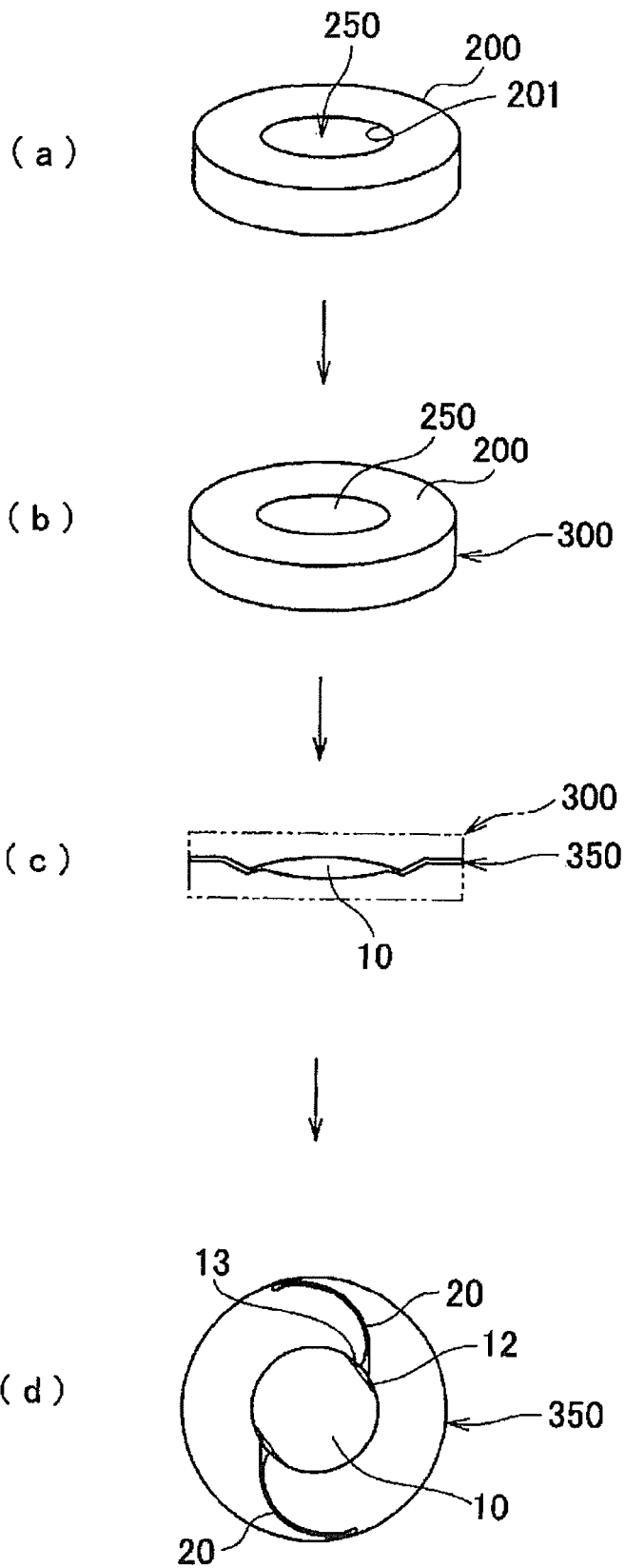
FIGS. 4(a) to (d) are explanatory views of a manufacturing step of the intraocular lens.
Figure 5:
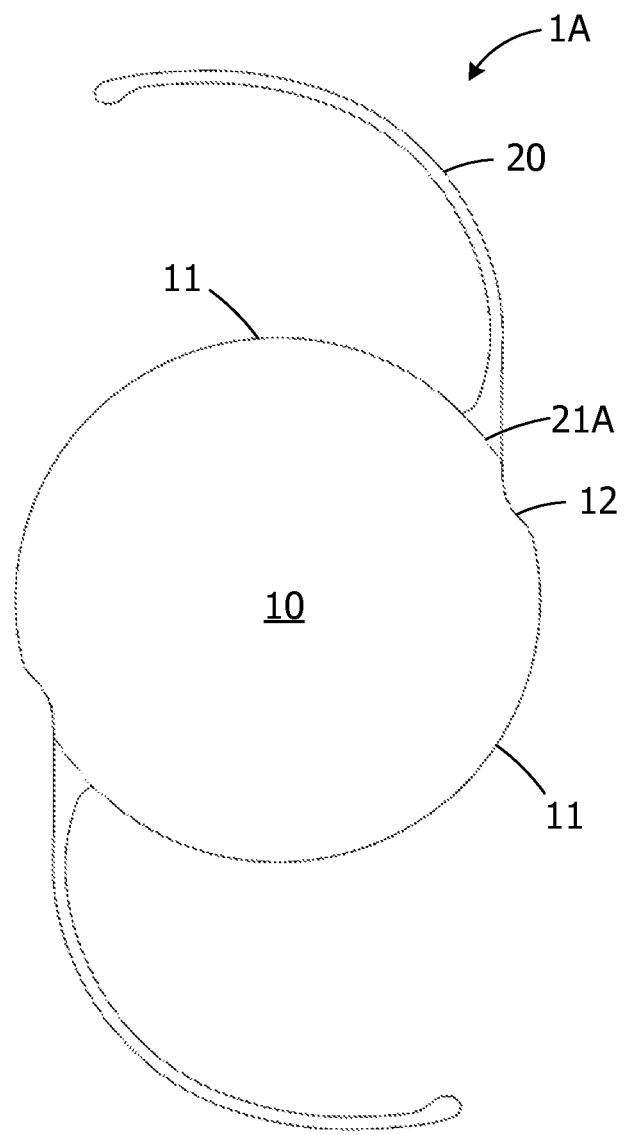
FIG. 5 is a front view of an intraocular lens according to an embodiment of the present invention.

1 Intraocular lens
10 Optical lens portion
11 Outer peripheral contour line
12, 13 Recess portion
20 Support arm portion
21A Root (initial root)
21B Root (substantial root)
22 Tip end
30 Convex curve

What is claimed is:

1. A foldable intraocular lens, comprising:
an optical lens portion having a center, an outer peripheral edge that defines a continuous convex curve, and only first and second indentations that are each closer than the continuous convex curve to the center;
a first haptic extending from the first indentation such that a first portion of the first haptic is closer to the center than the continuous convex curve, a second portion of the first haptic is farther from the center than the continuous convex curve, the first haptic has first and second side edges that both extend from the first portion of the first haptic to the second portion of the first haptic, and the first indentation is only associated with one of the first and second side edges of the first haptic;
a second haptic extending from the second indentation such that a first portion of the second haptic is closer to the center than the continuous convex curve, a second portion of the second haptic is farther from the center than the continuous convex curve, the second haptic has first and second side edges that both extend from the first portion of the second haptic to the second portion of the second haptic, and the second indentation is only associated with one of the first and second side edges of the second haptic;
wherein the optical lens portion and the first portions of the first and second haptics are formed from a first material, and at least a part of the second portions of the first and second haptics that are located adjacent to the first portions of the first and second haptics are formed from a second material that is harder than the first material.

2. A foldable intraocular lens as claimed in claim 1, wherein
the first material comprises acrylic material;
the second material comprises polymethylmethacrylate.

3. A foldable intraocular lens as claimed in claim 1, wherein
the continuous convex curve comprises a partial circle or a partial ellipse.

4. A foldable intraocular lens as claimed in claim 1, wherein
the optical lens portion includes an optical axis that passes through the center; and
the first portions of the first and second haptics define a width in a plane that is perpendicular to the optical axis that tapers inwardly.

5. A foldable intraocular lens as claimed in claim 1, wherein
a boundary is defined between the first material and the second material and the boundary has a curvature that corresponds to the continuous convex curve.

6. A foldable intraocular lens as claimed in claim 1, wherein
the first material comprises a foldable material.

7. A foldable intraocular lens as claimed in claim 1, wherein
the entire second portion of each of the first and second haptics is formed from a second material that is harder than the first material.

8. A foldable intraocular lens, comprising:
an optical lens portion having an optical axis, a center and first and second outer peripheral contours that together define a continuous convex curve that extends around the optical lens portion, the first and second outer peripheral contours each including first and second indentations that are each curved in shape and closer than the continuous convex curve to the center;
a first haptic adjacent to and between the first indentation of the first outer peripheral contour and the second indentation of the second outer peripheral contour, the first haptic defining a first contour line, which is contiguous with the first indentation of the first outer peripheral contour such that an edge in a plane that is perpendicular to the optical axis extends from the contour line, through the first indentation, and to the continuous convex curve, the edge being curved over the entire portion thereof that is coextensive with the first indentation of the first outer peripheral contour, the first haptic having a first haptic portion that abuts the optical lens portion and a second haptic portion that abuts and is located outward of the first haptic portion; and
a second haptic adjacent to and between the second indentation of the first outer peripheral contour and the first indentation of the second outer peripheral contour, the second haptic defining a first contour line, which is contiguous with the first indentation of the second outer peripheral contour such that an edge in a plane that is perpendicular to the optical axis extends from the contour line, through the second indentation, and to the continuous convex curve, the edge being curved over the entire portion thereof that is coextensive with the first indentation of the second outer peripheral contour, the second haptic having a first haptic portion that abuts the optical lens portion and a second haptic portion that abuts and is located outward of the first haptic portion;
wherein the optical lens portion and the first haptic portion of the first haptic are formed from a first material, and at least a part of the second haptic portion of the first haptic that is adjacent to the first haptic portion is formed from a second material that is harder than the first material; and
wherein the first haptic portion of the second haptic is formed from the first material, and at least a part of the second haptic portion of the second haptic that is adjacent to the first haptic portion is formed from the second material.

9. A foldable intraocular lens as claimed in claim 8, wherein
the first and second haptics are integral with the optical lens portion.

10. A foldable intraocular lens as claimed in claim 8, wherein
the continuous convex curve comprises a partial circle or a partial ellipse.

11. A foldable intraocular lens as claimed in claim 8, wherein
the first material comprises a foldable material.

12. A foldable intraocular lens as claimed in claim 8, wherein
the second haptic portion of the first and second haptics is located further from the center of the optical lens portion than the continuous convex curve.

13. A foldable intraocular lens as claimed in claim 8, wherein
the entire second haptic portion of the first and second haptics is formed from the second material.

14. A foldable intraocular lens as claimed in claim 8, wherein
the first haptic defines a second contour line which is contiguous with the second indentation of the second outer peripheral contour; and
the second haptic defining a second contour line, which is contiguous with the second indentation of the first outer peripheral contour.

* * * * *